United States Patent [19]
Bandman et al.

[11] Patent Number: 5,869,311
[45] Date of Patent: Feb. 9, 1999

[54] MITOCHONDRIAL PROCESSING PEPTIDASE SUBUNIT

[75] Inventors: Olga Bandman, Mountain View; Purvi Shah, Sunnyvale; Neil C. Corley, Mountain View, all of Calif.

[73] Assignee: Incyte Pharmaceuticals, Inc., Palo Alto, Calif.

[21] Appl. No.: 895,521

[22] Filed: Jul. 17, 1997

[51] Int. Cl.$^6$ .............................. C12N 15/09; C12N 9/14; C07K 14/435

[52] U.S. Cl. ................. 435/212; 435/252.3; 435/252.33; 435/254.11; 435/254.3; 435/325; 435/419; 435/320.1; 536/23.1; 536/23.2

[58] Field of Search .................................. 435/212, 252.3, 435/252.33, 254.11, 254.3, 325, 419, 320.1; 536/23.1, 23.2

[56] References Cited

PUBLICATIONS

Kitada S, et al., Molecular cloning of the smaller subunit (P52) of rat liver mitochondrial processing protease. Biochem Biophys Res Commun. 1993 Jan 15; 190(1:289–293, Jan. 15, 1993.

Kalousek F, et al. Uniform nomenclature of the mitochondrial peptidases cleaving precursors of mitochondrial proteins. Trends Biochem Sci. 1993 Jul; 18(7): 249, Jul. 1, 1993.

Niidome T, et al. Arginine residues in the extension peptide are required for cleavage of a precursor by mitochondrial processing peptidase. Demonstration using synthetic peptide as a substrate. J Biol Chem. 1994 Oct 7; 269(40): 24719–24722, Oct. 7, 1994.

Kitada S, et al. A putative metal–binding site in the beta subunit of rat mitochondrial processing peptidase is essential for its catalytic activity. J Biochem (Tokyo), 1995 Jun; 117(6): 1148–1150, Jun. 1, 1996.

Rawlings ND, et al. Homologues of insulinase, a new superfamily of metalloendopeptidases. Biochem J. 1991 Apr. 15; 275(Pt 2): 389–391, Apr. 15, 1991.

Paces, V. et al, "The β subunit of the mitochondrial processing peptidase from rat liver: Cloning and sequencing of a cDNA and comparison with a proposed family of metallopeptidases." *Proc. Natl. Acad. Sci. USA* (1993) 90:5355–5358 (GI 294589).

Hoffman, G.G. et al., "Complete Coding Sequence, Intron/Exon Organization, and Chromosomal Location of the Gene for the Core I Protein of Human Ubiquinol–Cytochome c Reductase." *J. Biol. Chem.* (1993) 268:21113–21119. (GI 1082896).

Kleiber, J. et al., "The general mitochondrial matrix processing protease from rat liver: Structural characterization of the catalytic subunit." *Proc. Natl. Acad. Sci. USA* (1990) 87:7978–7982.

Paces, V. et al., (GI 2984589) GenBank Sequence Database (Accession L12965), National Center for Biotechnology Information, National Library of Medicine, Bethesda, Maryland, 20894. No year provided.

Paces, V. et al., (GI 294588) GenBank Sequence Database (Accession L12965), National Center for Biotechnology Information, National Library of Medicine, Bethesda, Maryland, 20894. No year provided.

Hoffman, G.G. et al., (GI 1082896) GenBank Sequence Database (Accession A48043), National Center for Biotechnology Information, National Library of Medicine, Bethesda, Maryland, 20894. No year provided.

Hoffman, G.G. et al., (GI 349472) GenBank Sequence Database (Accession L16842), National Center for Biotechnology Information, National Library of Medicine, Bethesda, Maryland, 20894. No. year provided.

*Primary Examiner*—Keith D. Hendricks
*Assistant Examiner*—Bradley S. Mayhew
*Attorney, Agent, or Firm*—Incyte Pharmaceuticals, Inc.; Lucy J. Billings; Sheela Mohan-Peterson

[57] ABSTRACT

The invention provides a human mitochondrial processing peptidase subunit (MPPS-1) and polynucleotides which identify and encode MPPS-1. The invention also provides expression vectors, host cells, agonists, antibodies and antagonists. The invention also provides methods for treating disorders associated with expression of MPPS-1.

10 Claims, 11 Drawing Sheets

```
                                                          9                  18                 27              36              45             54
5' NCC TCT ACC TTC CTT CTA GCA GAA ATG GCG GCT GCG GCT CGA GTG TTG
                                    M   A   A   A   A   R   V   L 63                72             81             90             99            108
   TCA TCC GCG GCG CGG CGG CTC TGG GGT TTC AGC GAG AGT CTT CTA ATC CGA
    S   S   A   A   R   R   L   W   G   F   S   E   S   L   L   I   R 117               126            135            144            153           162
   GGC GCT GCG GGA CGG TCA TTA TAT TTT GGA GAG AAC AGA TTA AGA AGT ACA CAG
    G   A   A   G   R   S   L   Y   F   G   E   N   R   L   R   S   T   Q 171               180            189            198            207           216
   GCT GCT ACC CAA GTT CTG AAT GTT CCT GAA ACA AGA GTA ACA TGT TTA GAA
    A   A   T   Q   V   L   N   V   P   E   T   R   V   T   C   L   E 225               234            243            252            261           270
   AGT GGA CTC AGA GTA GCT TCG GAA GAC TCT GGG CTC TCA ACA GTT GGA
    S   G   L   R   V   A   S   E   D   S   G   L   S   T   V   G 279               288            297            306            315           324
   CTC TGG ATT GAT GCT GGA AGT AGA TAC GAA AAT GAG AAG AAC TGC ACA GTT GCA
    L   W   I   D   A   G   S   R   Y   E   N   E   K   N   G   T   A 333               342            351            360            369           378
   CAC TTT CTG GAG CAT ATG GCT TTC AAG GGC ACC AAG AAG AGA TCC CAG TTA GAT
    H   F   L   E   H   M   A   F   K   G   T   K   K   R   S   Q   L   D
```

FIGURE 1A

```
        387           396           405           414           423           432
CTG GAA CTT GAG ATT GAA AAT ATG GGT GCT CAT CTC AAT GCC TAT ACC TCC AGA
 L   E   L   E   I   E   N   M   G   A   H   L   N   A   Y   T   S   R 441           450           459           468           477           486
GAG CAG ACT GTA-TAC TAT GCC AAA GCA TTC TCT AAA GAC TTG CCA AGA GCT GTA
 E   Q   T   V   Y   Y   A   K   A   F   S   K   D   L   P   R   A   V 495           504           513           522           531           540
GAA ATT CTT GCT GAT ATA ATA CAA AAC AGC ACA TTG GGA GAA GCA GAG ATT GAA
 E   I   L   A   D   I   I   Q   N   S   T   L   G   E   A   E   I   E 549           558           567           576           585           594
CGT GAG CGT GGA GTA ATC CTT AGA GAG ATG CAG GAA GTT GAA ACC AAT TTA CAA
 R   E   R   G   V   I   L   R   E   M   Q   E   V   E   T   N   L   Q 603           612           621           630           639           648
GAA GTT GTT TTT GAT TAT CTT CAT GCC ACA GCT TAT CAA AAT ACT GCA CTT TGA
 E   V   V   F   D   Y   L   H   A   T   A   Y   Q   N   T   A   L   X 657           666           675           684           693           702
CGG ACA ATT TTT GGA CCA ACT GAA AAT ATC AAA TCT ATA AGT CGT AAG GAC TTA
 R   T   I   F   G   P   T   E   N   I   K   S   I   S   R   K   D   L 711           720           729           738           747           756
GTG GAT TAT ATA ACC ACA CAT TAT AAG GGG CCA AGA ATA GTG CTT GCT GCT GCT
 V   D   Y   I   T   T   H   Y   K   G   P   R   I   V   L   A   A   A
```

FIGURE 1B

```
       765         774         783         792         801         810
GGA GGT GTT TCC CAT GAT GAA TTG CTT GAC TTA GCA AAG TTT CAT TTC GGT GAC
 G   G   V   S   H   D   E   L   L   D   L   A   K   F   H   F   G   D 819         828         837         846         855         864
TCT TTA TGC ACA CAC AAA GGA GAA ATA CCA GCT CTG CCT CCC TGC AAA TTC ACA
 S   L   C   T   H   K   G   E   I   P   A   L   P   P   C   K   F   T 873         882         891         900         909         918
GGA AGT GAG ATT CGT GTG AGG GAT GAC AAG ATG CCT TTG GCG CAC CTT GCA ATA
 G   S   E   I   R   V   R   D   D   K   M   P   L   A   H   L   A   I 927         936         945         954         963         972
GCT GTT GAA GCT GTT GGT TGG GCA CAT CCA ACA ATC TGT CTC ATG GTT GCA
 A   V   E   A   V   G   W   A   H   P   T   I   C   L   M   V   A 981         990         999         1008        1017        1026
AAC ACG CTG ATT GGC AAC TGG GAT CGC TCT TTT GGG GGA ATG AAT TTA TCT
 N   T   L   I   G   N   W   D   R   S   F   G   G   M   N   L   S 1035        1044        1053        1062        1071        1080
AGC AAG CTG GCC CAG CTC ACT TGT CAT GGC AAT CTT TGC CAT AGC TTT CAG TCT
 S   K   L   A   Q   L   T   C   H   G   N   L   C   H   S   F   Q   S 1089        1098        1107        1116        1125        1134
TTC AAC ACT TCC TAC ACA GAT ACA GGA TTA TGG GGA CTG TAT ATG GTT TGT GAA
 F   N   T   S   Y   T   D   T   G   L   W   G   L   Y   M   V   C   E
```

FIGURE 1C

```
      1143             1152            1161            1170            1179            1188
TCA TCC ACT GTT GCA GAC ATG CTA CAT GTT GTT CAA AAA GAA TGG ATG CGA CTC
 S   S   T   V   A   D   M   L   H   V   V   Q   K   E   W   M   R   L 1197             1206            1215            1224            1233            1242
TGT ACA AGT GTC ACA GAA AGT GAT GTT GCA CGA GCC AGA AAT CTT CTG AAA ACA
 C   T   S   V   T   E   S   D   V   A   R   A   R   N   L   L   K   T 1251             1260            1269            1278            1287            1296
AAC ATG TTG CAG CTT GAT GGT TCA ACT CCA ATT TGT GAA GAT ATT GGT AGG
 N   M   L   Q   L   D   G   S   T   P   I   C   E   D   I   G   R 1305             1314            1323            1332            1341            1350
CAA ATG TTA TGC TAT AAT AGA AGG ATT CCC ATC CCT GAG CTT GAA GCA AGA ATT
 Q   M   L   C   Y   N   R   R   I   P   I   P   E   L   E   A   R   I 1359             1368            1377            1386            1395            1404
GAT GCT GTG AAT GCT GAG ACA ATT CGA GAA GTA TGT ACC AAA TAC ATT TAT AAT
 D   A   V   N   A   E   T   I   R   E   V   C   T   K   Y   I   Y   N 1413             1422            1431            1440            1449            1458
AGT CCA GCT ATT GCT GTT GGT CCC ATT AAG CAA CTA CCA GAT TTT AAA
 R   S   P   A   I   A   V   G   P   I   K   Q   L   P   D   F   K 1467             1476            1485            1494            1503            1512
CAG ATA CGC AGT AAC ATG TGT TGG CTT CGT GAT TAA AAT GCT CCT AAT CAA GAT
 Q   I   R   S   N   M   C   W   L   R   D
```

FIGURE 1D

```
     1521           1530          1539          1548          1557          1566
TGT TTG AAC ACA TGT ATT TAT AAA ACA GAG CTA GAG AAA AAT AAA AAT GAA CAT 1575           1584          1593          1602          1611          1620
GTA TAT ACA TTT GGA AAT TTG AAT TAA ATA CTG TAT CAT ACT TTC AAA GGA TAA 1629           1638          1647          1656          1665          1674
AAA GAC TAC CCC TCT GAA GGT TGT TTT GTA TTA ATG GTC AGT CTT TGT TCT CTG 1683           1692          1701          1710          1719          1728
AGA AAT TAT GTT GGA AGC ATA CTT TCA AAT TAT TAC CAT GAG TAT AAT TTT 1737           1746          1755          1764          1773          1782
AAG AAT GAA AAT GTT TAC AGT ATT TTC AGT TTT ATT ATA AAA ATG CAC ACA CAA

AAA AAA AA 3'
```

FIGURE 1E

```
  1  M A A A A A R V V L S S A A R R R L W G F S E S L L I R G A A G R S L Y F G E N  MPPS-1
  1  M A A A A A V S R T L L P V A G R R L W G F T R R L P L R A A A Q P L Y F G G D  g294589
  1  M A A S V V C R A A T A G A Q V L L R A R R S P A L L R T P A - - - - - - - - -  g1082896

41  R L R S T Q A A T Q V V L N V P E T R V T C L E S G L R V A S E D S G L S T C T  MPPS-1
 41  R L R S T Q A A P Q V V L N V P E T Q V T C L E N G L R V A S E N S G I S T C T  g294589
 32  - L R S T A T F A Q F V P E T Q V S L L D N G L R V A S E Q S Q P T C T          g1082896

81  V G L W I D A G S R Y E N E K N N G T A H F L E H M A F K G T K K R S Q L D L E  MPPS-1
 81  V G L W I D A G S R Y E N E K N N G T A H F L E H M A F K G T K K R S Q L D L E  g294589
 71  V G V W I D V G S R F E T E K N N G A G Y F L E H L A F K G T K N R P G S A L E  g1082896

121  L E I E N M G A H L N A Y T S R E Q T V V Y Y A K A F S K D L P R A V E I L A D I  MPPS-1
121  L E I E N M G A H L N A Y T S R E Q T V V Y Y A K A F S K D L P R A V E I L A D I  g294589
111  K E V E S M G A H L N A Y S T R E H T A Y Y I K A L S K D L P K A V E L L G D I  g1082896

161  I Q N S T L G E A E I E R E R G V I L R E M Q E V E T N L Q E V V F D Y L H A T  MPPS-1
161  I Q N S T L G E A E I E R E R G V I L R E M Q E V E T N L Q E V V F D Y L H A T  g294589
151  V Q N C S L E D S Q I E K E R D V I L R E M Q E N D A S M R D V V F N Y L H A T  g1082896
```

```
201 A Y Q N T A L X R T I F G P T E N I K S I S R K D L V D Y I T T H Y K G P R I V   MPPS-1
201 A Y Q N T A L G R T I L G P T E N I K S I S R K D L V D Y I T T H Y K G P R I V   g294589
191 A F Q G T P L A Q A V E G P S E N V R K L S R A D L T E Y L S T H Y K A P R M V   g1082896

241 L A A A G G V S H D E L L D L A K F H F G D - S L C T H K G E I P A L P P C K F   MPPS-1
241 L A A A G G V C H N E L E L A K F H F G D - S L C A H K G D V P A L P P C K F   g294589
231 L A A A G G V E H Q Q L L D L A Q K H L G G I P W T Y A E D A V P T L T P C R F   g1082896

280 T G S E I R V R D D K M P L A H L A I A V E A V G W A H P D T I C L M V A N T L   MPPS-1
280 T G S E I R V R D D K M P L A H L A V A I E A V G W T H P D T I R L M V A N T L   g294589
271 T G S E I R H R D D A L P F F A H V A I A V E G P G W A S P D S V A L Q V A N A I   g1082896

320 I G N W D R S F G G G M N L S S K L A Q L T C H G N L C H S F Q S F N T S Y T D   MPPS-1
320 I G N W D R S F G G G M N L S S K L A Q L T C H G N L C H S F Q S F N T S Y T D   g294589
311 I G H Y D C T Y G G G V H L S S P L A S G A V A N K L C Q S F Q T F S I C Y A E   g1082896

360 T G L W G L Y M V C E S S T V A D M L H V V Q K E W M R L C T S V T E S D V A R   MPPS-1
360 T G L W G L Y M V C E Q A T V A D M L H A V Q K E W M R L C T A V S E S E V A R   g294589
351 T G L L G A H F V C D R M K I D D M M F V L Q Q W M R L C T S A T E S E V A R   g1082896
```

```
400  A R N L L K T N M L L Q L D G S T P I C E D I G R Q M L C Y N R R I P I P E L E  MPPS-1
400  A K N L L K T N M L L Q L D G S T P I C E D I G R Q M L C Y N R R I P I P E L E  g294589
391  G K N I L R N A L V S H L D G T T P V C E D I G R S L L T Y G R R I P L A E W E  g1082896

440  A R I D A V N A E T I R E V C T K Y I Y N R S P A I A A V G P I K Q L P D F K Q  MPPS-1
440  A R I D A V D A E M V R E V C T K Y I Y G K S P A I A A L G P I E R L P D F N Q  g294589
431  S R I A E V D A S V V R E I C S K Y I Y D Q C P A V A G Y G P I E Q L P D Y N R  g1082896

480  I R S N M C W L R D     MPPS-1
480  I C S N M R W T R D    g294589
471  I R S G M F W L R F    g1082896
```

FIGURE 2C

MITOCHONDRIAL PROCESSING PEPTIDASE SUBUNIT

FIELD OF THE INVENTION

This invention relates to nucleic acid and amino acid sequences of a mitochondrial processing peptidase subunit and to the use of these sequences in the diagnosis, prevention, and treatment of smooth muscle disorders, neurological disorders, and cancer.

BACKGROUND OF THE INVENTION

Mitochondria are the primary sites of energy production in cells. Energy production occurs through the action of a series of enzyme complexes called the mitochondrial electron transport (or respiratory) chain. These complexes are responsible for: 1) the transport of electrons from NADH to oxygen and, 2) the coupling of oxidation to synthesis of ATP (oxidative phosphorylation). ATP then provides the primary source of energy for driving a cell's many energy-requiring reactions.

Most mitochondrial proteins are the products of nuclear genes and are imported into the mitochondria from the cytosol following their synthesis. Targeting of these proteins to mitochondria is achieved by an N-terminal leader (or signal) peptide of 10 to 70 amino acid residues which contains many positively charged amino acids. Once these precursor proteins are localized in the mitochondria, the leader peptide is cleaved by a signal peptidase to generate the mature protein. Most leader peptides are removed in a one step process by a protease termed mitochondrial processing peptidase (MPP) (Paces, V. et al. (1993) Proc. Natl. Acad. Sci. 90:5355–58). In some cases a two-step process occurs in which MPP generates an intermediate precursor form which is cleaved by a second enzyme, mitochondrial intermediate peptidase, to generate the mature protein.

MPP isolated from *Neurospora crassa* is a complex consisting of two dissociable components. The larger component has catalytic activity and has been called MPP; and the smaller component increases the activity of the complex and is called protease enhancing peptidase (PEP). MPP from *Saccharomyces cerevisiae* and rat liver is a heterodimer consisting of two dissimilar subunits, alpha (~55 kDa) and beta (~55 kDa) (Paces, et al. supra). In these species, it has not been determined whether the protease activity lies solely in the dimer or in a single subunit. The alpha-subunit of rat liver MPP is 36% identical to the large subunit (MPP) of *N. crassa*. The beta-subunit of rat liver MPP, beta-MPP, is most closely related to the smaller subunit of *S. cerevisiae* MPP (45% identity) and to *N. crassa* PEP (52% identity). Rat liver beta-MPP is also homologous (55% identity) to the core I protein from human ubiquinol-cytochrome c reductase (Hoffman, G. G. et al. (1993) J. Biol. Chem. 268:21113–19). Ubiquinol-cytochrome c reductase is one of the key enzyme complexes in the respiratory chain. It consists of 10–11 subunits, two of which are designated core I and core II proteins. The exact function of these two proteins is not known, but in yeast they appear to be necessary for assembly of the complex (Hoffman et al. supra). Although the core I protein of ubiquinol-cytochrome c reductase and PEP are identical proteins in *N. crassa*, the structurally homologous core I and beta-MPP proteins of yeast, rat, and human are genetically distinct.

Rat liver beta-MPP is 489 amino acids in length and is characterized by a 45-amino acid leader peptide that is positively charged and has a predicted signal peptidase cleavage site sequence, $RST_{45}QA$. Paces et al.(supra) suggest that, after being imported into the mitochondria, beta-MPP is cleaved by pre-existing MPP. An alpha-helical structure is predicted in the region between amino acids 165 and 205 of beta-MPP. The first part of this region, residues 168–186, is highly charged with several glutamate and arginine residues. This highly charged, amphiphilic helix, that is present in alpha-MPP as well, is believed to participate in binding of MPP to the positively charged, leader peptide substrates. An additional feature of beta-MPP and its homologs is the presence of one or two possible divalent metal-binding sites characteristic of metallopeptidases. Residues $H_{101}$, $E_{181}$, and $H_{198}$ are believed to cooperate in binding of divalent metals such as $Zn^{2+}$ or $Mn^{2+}$, and the sequence $H_{101}FLEH$, unique to the rat liver beta-MPP, is also a potential metal-binding site (Paces, et al. supra).

The discovery of a new mitochondrial processing peptidase subunit and the polynucleotides encoding it satisfies a need in the art by providing new compositions which are useful in the diagnosis, prevention and treatment of smooth muscle disorders, neurological disorders, and cancer.

SUMMARY OF THE INVENTION

The invention features a substantially purified polypeptide, mitochondrial processing peptidase subunit (MPPS-1), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof and a composition comprising said polynucleotide sequence. The invention also provides a polynucleotide sequence which hybridizes under stringent conditions to the polynucleotide sequence encoding the amino acid sequence SEQ ID NO:1, or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2 or variants thereof. In addition, the invention provides a polynucleotide sequence which hybridizes under stringent conditions to the polynucleotide sequence of SEQ ID NO:2.

In another aspect the invention provides a composition comprising an isolated and purified polynucleotide sequence comprising the complement of SEQ ID NO:2, or fragments or variants thereof. The invention also provides a polynucleotide sequence comprising the complement of SEQ ID NO:2.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding MPPS-1 under conditions suitable for the expression of the polypeptide; and b) recovering the polypeptide from the host cell culture.

The invention also provides a pharmaceutical composition comprising a substantially purified MPPS-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising at least a fragment of the amino acid sequence of SEQ ID NO:1.

Still further, the invention provides a purified agonist of the polypeptide of SEQ ID NO:1.

The invention also provides a method for treating or preventing a smooth muscle disorder comprising administering to a subject in need of such treatment an effective amount of a pharmaceutical composition comprising purified MPPS-1.

The invention also provides a method for treating or preventing a neurological disorder comprising administering to a subject in need of such treatment an effective amount of a pharmaceutical composition comprising purified MPPS-1.

The invention also provides a method for treating or preventing cancer comprising administering to a subject in need of such treatment an effective amount of a purified antagonist of MPPS-1.

The invention also provides a method for detecting a polynucleotide which encodes MPPS-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding MPPS-1 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of MPPS-1. The alignment was produced using MacDNASIS PRO™ software (Hitachi Software Engineering Co. Ltd. San Bruno, Calif.).

FIGS. 2A, 2B, and 2C show the amino acid sequence alignments among MPPS-1 (457485; SEQ ID NO:1), the beta-subunit of mitochondrial processing peptidase from rat, beta-MPP (GI 294589; SEQ ID NO:3) and human ubiquinol-cytochrome-c reductase, core I protein (GI 1082896; SEQ ID NO:4), produced using the multisequence alignment program of DNASTAR™ software (DNASTAR Inc, Madison, Wis.).

DESCRIPTION OF THE INVENTION

Figure 3A:
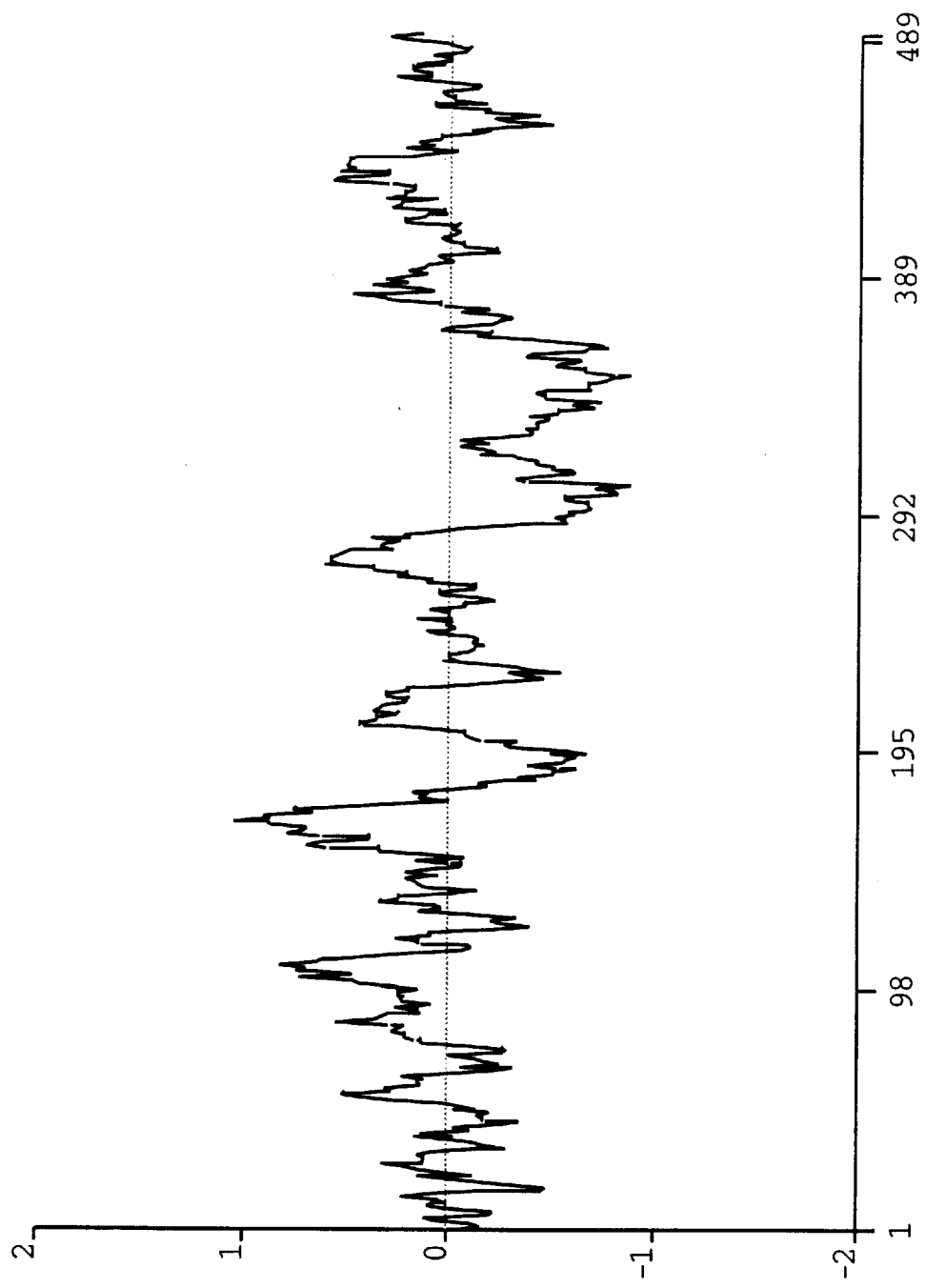
FIGS. 3A, 3B, and 3C show the hydrophobicity plots for MPPS-1 (SEQ ID NO:1), rat beta-MPP (SEQ ID NO:3), and human core I protein (SEQ ID NO:4), respectively; the positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

MPPS-1, as used herein, refers to the amino acid sequences of substantially purified MPPS-1 obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to MPPS-1, increases or prolongs the duration of the effect of MPPS-1. Agonists may include proteins, nucleic acids, carbohydrates, or any other molecules which bind to and modulate the effect of MPPS-1.

An "allele" or "allelic sequence", as used herein, is an alternative form of the gene encoding MPPS-1. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding MPPS-1 as used herein include those with deletions, insertions, or substitutions of different nucleotides resulting in a polynucleotide that encodes the same or a functionally equivalent MPPS-1. Included within this definition are polymorphisms which may or may not be readily detectable using a particular oligonucleotide probe of the polynucleotide encoding MPPS-1, and improper or unexpected hybridization to alleles, with a locus other than the normal chromosomal locus for the polynucleotide sequence encoding MPPS-1. The encoded protein may also be "altered" and contain deletions, insertions, or substitutions of amino acid residues which produce a silent change and result in a functionally equivalent MPPS-1. Deliberate amino acid substitutions may be made on the basis of similarity in polarity, charge, solubility, hydrophobicity, hydrophilicity, and/or the arnphipathic nature of the residues as long as the biological or immunological activity of MPPS-1 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of MPPS-1 are preferably about 5 to about 15 amino acids in length and retain the biological activity or the immunological activity of MPPS-1. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to MPPS-1, decreases the amount or the duration of the effect of the biological or immunological activity of MPPS-1. Antagonists may include proteins, nucleic acids, carbohydrates, antibodies or any other molecules which decrease the effect of MPPS-1.

As used herein, the term "antibody" refers to intact molecules as well as fragments thereof, such as Fa, F(ab')$_2$, and Fv, which are capable of binding the epitopic determinant. Antibodies that bind MPPS-1 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic MPPS-1, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding MPPS-1 (SEQ ID NO:1) or fragments thereof (e.g., SEQ ID NO:2 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding MPPS-1 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to MPPS-1 or the encoded MPPS-1. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of MPPS-1. For example, modulation may cause an increase or a decrease in protein activity, binding characteristics, or any other biological, functional or immunological properties of MPPS-1.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray.

As used herein, oligonucleotide is substantially equivalent to the terms "amplimers","primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length MPPS-1 and fragments thereof.

The term "sample", as used herein, is used in its broadest sense. A biological sample suspected of containing nucleic acid encoding MPPS-1, or fragments thereof, or MPPS-1 itself may comprise a bodily fluid, extract from a cell, chromosome, organelle, or membrane isolated from a cell, a cell, genomic DNA, RNA, or cDNA(in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of MPPS-1, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

THE INVENTION

The invention is based on the discovery of a new human mitochondrial processing peptidase subunit (hereinafter referred to as "MPPS-1"), the polynucleotides encoding MPPS-1, and the use of these compositions for the diagnosis, prevention, or treatment of smooth muscle disorders, neurological disorders, and cancer.

Nucleic acids encoding the MPPS-1 of the present invention were first identified in Incyte Clone 1593490 from the brain cDNA library (BRAINOT14) using a computer search for amino acid sequence alignments. A consensus sequence, SEQ ID NO:2, was derived from the following overlapping and/or extended nucleic acid sequences: Incyte Clones 449760 and 450999/TLYMNOT02, 1234665/LUNGFET03, 1377691/LUNGNOT10, 1593490/BRAINOT14, and 1873221/LEUKNOT02.

Figure 3B:
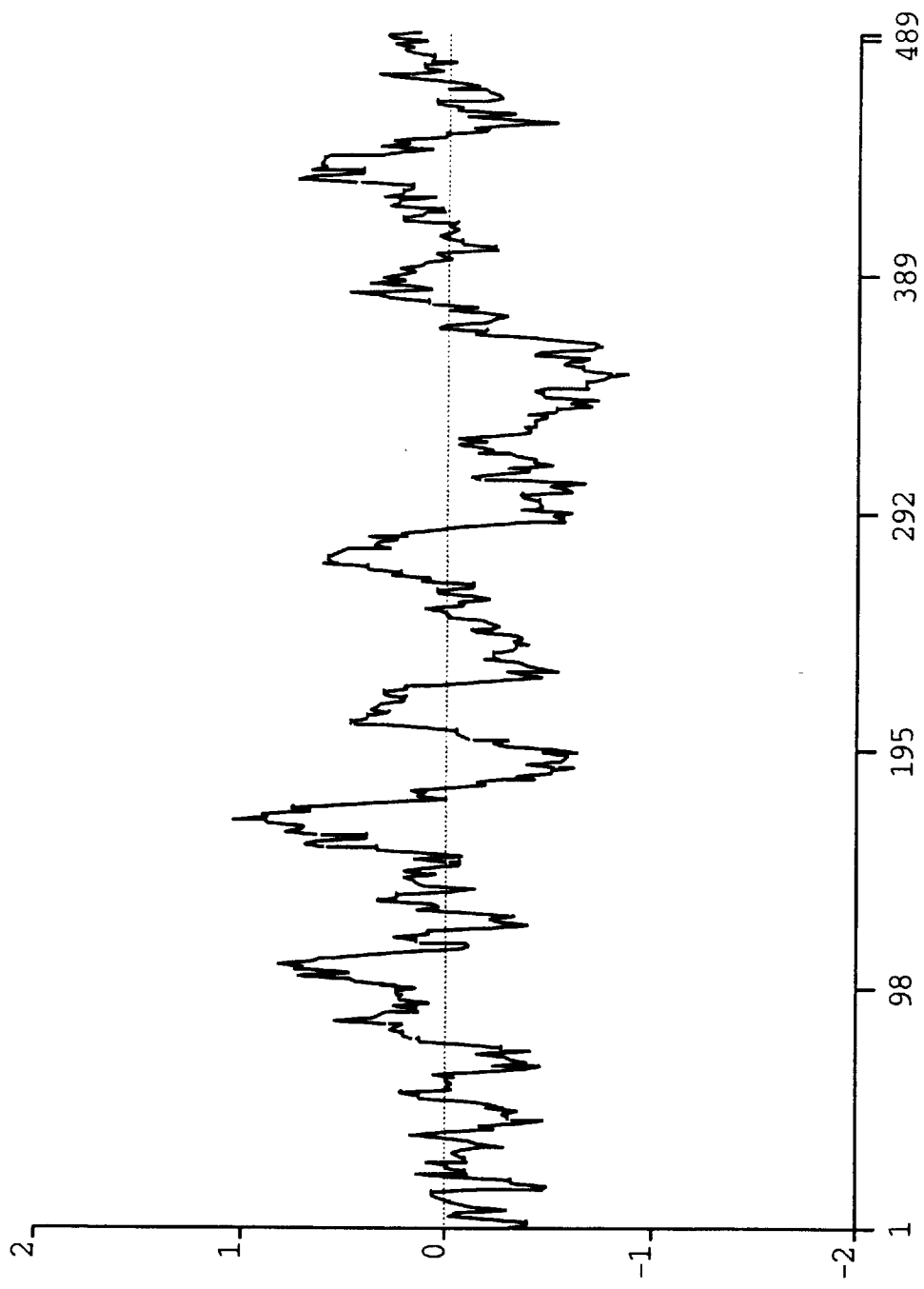
Figure 3C:
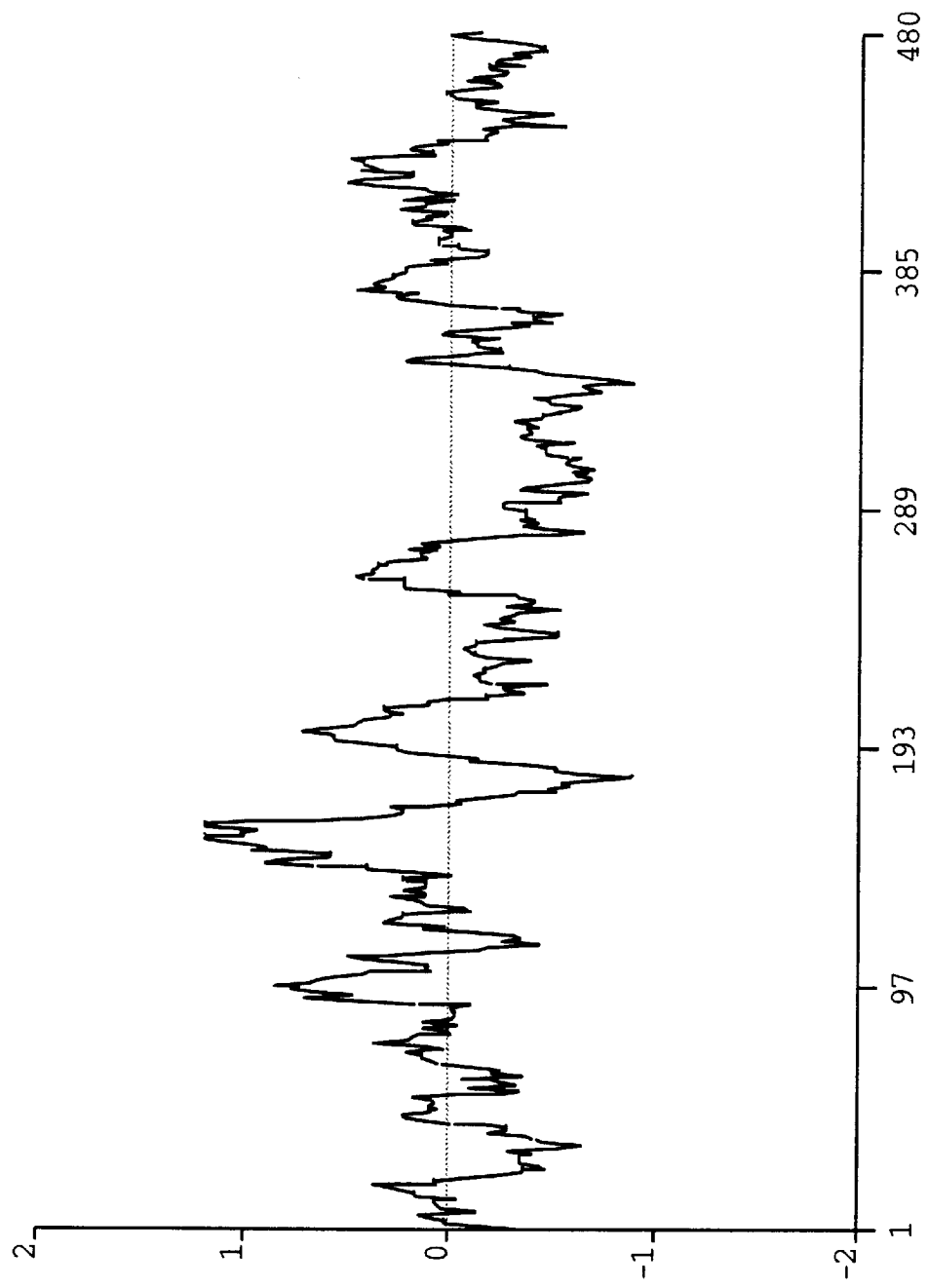

In one embodiment, the invention encompasses a polypeptide comprising the amino acid sequence of SEQ ID NO:1, as shown in FIG. 1. MPPS-1 is 489 amino acids in length and has potential N-linked glycosylation sites at residues $N_{97}$, $N_{163}$, $N_{332}$, and $N_{354}$. Cysteine residues representing potential intramolecular disulfide bridging sites are found at $C_{62}$, $C_{79}$, $C_{265}$, $C_{277}$, $C_{312}$, $C_{369}$, $C_{428}$, and $C_{454}$. Residues $M_1$–$T_{45}$ represent a potential mitochondrial signal peptide with seven positively charged arginine residues and a predicted signal peptidase cleavage site sequence at $RST_{45}QA$. The sequence between residues $T_{165}$ and $T_{205}$ represents a potential alpha-helix, that is highly charged with seven glutamate and three arginine residues, characteristic of a potential binding site for leader peptide substrates. Residues $H_{101}$, $E_{181}$, and $H_{198}$ are potential divalent metal-binding sites as is the sequence $H_{101}FLEH$. As shown in FIG. 2, MPPS-1 has chemical and structural homology with rat beta-MPP (GI 294589; SEQ ID NO:3) and human core I protein (GI 1082896; SEQ ID NO:4). In particular, MPPS-1 shares 89% and 58% identity with beta-MPP and core I protein, respectively. The four N-linked glycosylation sites found in MPPS-1 are shared by one or both of rat beta-MPP and human core I protein. All but one of the eight cysteine residues ($C_{312}$) found in MPPS-1 are also shared by one or both of beta-MPP and core I protein. The positively charged, alpha-helical region between residues $T_{165}$ and $T_{205}$ in MPPS-1 is found in rat beta-MPP. The potential metal binding sequence at $H_{101}FLEH$ in MPPS-1 is shared by rat beta-MPP and the additional potential metal binding residues at $E_{181}$, and $H_{198}$ are shared by all three proteins. As illustrated by FIGS. 3A, 3B, and 3C, MPPS-1, rat beta-MPP, and human core I protein have rather similar hydrophobicity plots. Northern analysis shows the expression of this sequence in various libraries, at least 43% of which are immortalized or cancerous, at least 33% of which are associated with smooth muscle tissues, and at least 16% of which are associated with the brain and neural tissue.

The invention also encompasses MPPS-1 variants. A preferred MPPS-1 variant is one having at least 80%, and more preferably at least 90%, amino acid sequence identity to the MPPS-1 amino acid sequence (SEQ ID NO:1) and which retains at least one biological, immunological or other functional characteristic or activity of MPPS-1. A most preferred MPPS-1 variant is one having at least 95% amino acid sequence identity to SEQ ID NO:1.

The invention also encompasses polynucleotides which encode MPPS-1. Accordingly, any nucleic acid sequence which encodes the amino acid sequence of MPPS-1 can be used to produce recombinant molecules which express MPPS-1. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of nucleotide sequences encoding MPPS-1, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring MPPS-1, and all such variations are to be considered as being specifically disclosed.

Although nucleotide sequences which encode MPPS-1 and its variants are preferably capable of hybridizing to the nucleotide sequence of the naturally occurring MPPS-1 under appropriately selected conditions of stringency, it may be advantageous to produce nucleotide sequences encoding MPPS-1 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding MPPS-1 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode MPPS-1 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding MPPS-1 or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding MPPS-1 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode MPPS-1 may be used in recombinant DNA molecules to direct expression of MPPS-1, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express MPPS-1.

As will be understood by those of skill in the art, it may be advantageous to produce MPPS-1-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter MPPS-1 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding MPPS-1 may be ligated to a heterologous sequence to encode a fusion protein. For example, to screen peptide libraries for inhibitors of MPPS-1 activity, it may be useful to encode a chimeric MPPS-1 protein that can be recognized by a commercially available antibody. A fusion protein may also be engineered to contain a cleavage site located between the MPPS-1 encoding sequence and the heterologous protein sequence, so that MPPS-1 may be cleaved and purified away from the heterologous moiety.

In another embodiment, sequences encoding MPPS-1 may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of MPPS-1, or a fragment thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) Proteins, Structures and Molecular Principles, W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of MPPS-1, or any part thereof, may be altered during direct synthesis and/or combined using chemical methods with sequences from other proteins, or any part thereof, to produce a variant polypeptide.

In order to express a biologically active MPPS-1, the nucleotide sequences encoding MPPS-1 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding MPPS-1 and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.

A variety of expression vector/host systems may be utilized to contain and express sequences encoding MPPS-1. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding MPPS-1, vectors based on SV40 or EBV may be used with an appropriate selectable marker.

In bacterial systems, a number of expression vectors may be selected depending upon the use intended for MPPS-1. For example, when large quantities of MPPS-1 are needed for the induction of antibodies, vectors which direct high level expression of fusion proteins that are readily purified may be used. Such vectors include, but are not limited to, the multifunctional E. coli cloning and expression vectors such as Bluescript® (Stratagene), in which the sequence encoding MPPS-1 may be ligated into the vector in frame with sequences for the amino-terminal Met and the subsequent 7 residues of 13β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding MPPS-1 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196.

An insect system may also be used to express MPPS-1. For example, in one such system, Autographa californica nuclear polyhedrosis virus (AcNPV) is used as a vector to express foreign genes in Spodoptera frugiperda cells or in Trichoplusia larvae. The sequences encoding MPPS-1 may be cloned into a non-essential region of the virus, such as the polyhedrin gene, and placed under control of the polyhedrin promoter. Successful insertion of MPPS-1 will render the polyhedrin gene inactive and produce recombinant virus lacking coat protein. The recombinant viruses may then be used to infect, for example, S. frugiperda cells or Trichoplusia larvae in which MPPS-1 may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding MPPS-1 may be ligated into an adenovirus transcription/translation complex consisting of the late promoter and tripartite leader sequence. Insertion in a non-essential E1 or E3 region of the viral genome may be used to obtain a viable virus which is capable of expressing MPPS-1 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding MPPS-1. Such signals include the ATG initiation codon and adjacent sequences. In cases where sequences encoding MPPS-1, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express MPPS-1 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G–418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding MPPS-1 is inserted within a marker gene sequence, transformed cells containing sequences encoding MPPS-1 can be identified by the absence of marker gene function. Alternatively, a marker gene can be placed in tandem with a sequence encoding MPPS-1 under the control of a single promoter. Expression of the marker gene in response to induction or selection usually indicates expression of the tandem gene as well.

Alternatively, host cells which contain the nucleic acid sequence encoding MPPS-1 and express MPPS-1 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding MPPS-1 can be detected by DNA-DNA or DNA-RNA hybridization or amplification using probes or fragments or fragments of polynucleotides encoding MPPS-1. Nucleic acid amplification based assays involve the use of oligonucleotides or oligomers based on the sequences encoding MPPS-1 to detect transformants containing DNA or RNA encoding MPPS-1.

A variety of protocols for detecting and measuring the expression of MPPS-1, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on MPPS-1 is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding MPPS-1 include oligolabeling, nick translation, end-labeling or PCR amplification using a labeled nucleotide. Alternatively, the sequences encoding MPPS-1, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding MPPS-1 may be cultured under conditions suitable for the expression and recovery of the protein from cell culture. The protein produced by a transformed cell may be secreted or contained intracellularly depending on the sequence and/ or the vector used. As will be understood by those of skill in the art, expression vectors containing polynucleotides which encode MPPS-1 may be designed to contain signal sequences which direct secretion of MPPS-1 through a prokaryotic or eukaryotic cell membrane. Other constructions may be used to join sequences encoding MPPS-1 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and MPPS-1 may be used to facilitate purification. One such expression vector provides for expression of a fusion protein containing MPPS-1 and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3:263–281) while the enterokinase cleavage site provides a means for purifying MPPS-1 from the fusion protein. A discussion of vectors which contain fusion proteins is provided in Kroll, D. J. et al. (1993; DNA Cell Biol. 12:441–453).

In addition to recombinant production, fragments of MPPS-1 may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of MPPS-1 may be chemically synthesized separately and combined using chemical methods to produce the full length molecule.

THERAPEUTICS

Chemical and structural homology exists between/among MPPS-1, the beta-subunit of mitochondrial processing peptidase from rat (GI 294589; SEQ ID NO:3), and human ubiquinol-cytochrome-c reductase, core I protein (GI 1082896; SEQ ID NO:4). In addition, MPPS-1 is expressed in cancerous tissues, smooth muscle tissues, and brain and neural tissues. Therefore, MPPS-1 appears to play a role in cancer, smooth muscle disorders, and neurological disorders.

A decrease in the level or activity of MPPS-1 appears to be associated with smooth muscle disorders. Therefore, in one embodiment, MPPS-1 or a fragment or derivative thereof may be administered to a subject to treat a smooth muscle disorder. A smooth muscle disorder is defined as any impairment or alteration in the normal action of smooth muscle and may include, but is not limited to, angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia. Smooth muscle includes, but is not limited to, that of the blood vessels, gastrointestinal tract, heart, and uterus.

In another embodiment, a vector capable of expressing MPPS-1, or a fragment or a derivative thereof, may also be administered to a subject to treat a smooth muscle disorder including, but not limited to, those described above.

In another embodiment, an agonist which modulates the activity of MPPS-1 may also be administered to a subject to treat a smooth muscle disorder including, but not limited to, those described above.

A decrease in the level or activity of MPPS-1 also appears to be associated with neurological disorders. Therefore, in another embodiment, MPPS-1 or a fragment or derivative thereof may be administered to a subject to treat a neurological disorder. Such disorders include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

In another embodiment, a vector capable of expressing MPPS-1, or a fragment or a derivative thereof, may also be administered to a subject to treat a neurological disorder including, but not limited to, those described above.

In another embodiment, an agonist which modulates the activity of MPPS-1 may also be administered to a subject to treat a neurological disorder including, but not limited to, those described above.

An increase in the level or activity of MPPS-1 appears to be associated with cancer. Therefore, in another embodiment, an antagonist of MPPS-1 may be administered to a subject to prevent or treat cancer. Cancers may include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds MPPS-1 may be used directly as an antagonist or indirectly as a targeting or delivery mechanism for bringing a pharmaceutical agent to cells or tissue which express MPPS-1.

In another embodiment, a vector expressing the complement of the polynucleotide encoding MPPS-1 may be administered to a subject to treat or prevent cancer including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of MPPS-1 may be produced using methods which are generally known in the art. In particular, purified MPPS-1 may be used to produce antibodies or to screen libraries of pharmaceutical agents to identify those which specifically bind MPPS-1.

Antibodies to MPPS-1 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with MPPS-1 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to MPPS-1 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of MPPS-1 amino acids may be fused with those of another protein such as keyhole limpet hemocyanin and antibody produced against the chimeric molecule.

Monoclonal antibodies to MPPS-1 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce MPPS-1-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for MPPS-1 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between MPPS-1 and its specific antibody. A two-site, monoclonal-based immunoassay utilizing monoclonal antibodies reactive to two non-interfering MPPS-1 epitopes is preferred, but a competitive binding assay may also be employed (Maddox, supra).

In another embodiment of the invention, the polynucleotides encoding MPPS-1, or any fragment or complement thereof, may be used for therapeutic purposes. In one aspect, the complement of the polynucleotide encoding MPPS-1 may be used in situations in which it would be desirable to block the transcription of the mRNA. In particular, cells may be transformed with sequences complementary to polynucleotides encoding MPPS-1. Thus, complementary molecules or fragments may be used to modulate MPPS-1 activity, or to achieve regulation of gene function. Such technology is now well known in the art, and sense or antisense oligonucleotides or larger fragments, can be designed from various locations along the coding or control regions of sequences encoding MPPS-1.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding MPPS-1. These techniques are described both in Sambrook et al. (supra) and in Ausubel et al. (supra).

Genes encoding MPPS-1 can be turned off by transforming a cell or tissue with expression vectors which express high levels of a polynucleotide or fragment thereof which encodes MPPS-1. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding MPPS-1 (signal sequence, promoters, enhancers, and introns). Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding MPPS-1.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding MPPS-1. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of MPPS-1, antibodies to MPPS-1, mimetics, agonists, antagonists, or inhibitors of MPPS-1. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of MPPS-1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example MPPS-1 or fragments thereof, antibodies of MPPS-1, agonists, antagonists or inhibitors of MPPS-1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind MPPS-1 may be used for the diagnosis of conditions or diseases characterized by expression of MPPS-1, or in assays to monitor patients being treated with MPPS-1, agonists, antagonists or inhibitors. The antibodies useful for diagnostic purposes may be prepared in the same manner as those described above for therapeutics. Diagnostic assays for MPPS-1 include methods which utilize the antibody and a label to detect MPPS-1 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring MPPS-1 are known in the art and provide a basis for diagnosing altered or abnormal levels of MPPS-1 expression. Normal or standard values for MPPS-1 expression are established by combining body fluids or cell extracts taken from normal mammalian subjects, preferably human, with antibody to MPPS-1 under conditions suitable for complex formation. The amount of standard complex formation may be quantified by various methods, but preferably by photometric, means. Quantities of MPPS-1 expressed in subject, control and disease, samples from biopsied tissues are compared with the standard values. Deviation between standard and subject values establishes the parameters for diagnosing disease.

In another embodiment of the invention, the polynucleotides encoding MPPS-1 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of MPPS-1 may be correlated with disease. The diagnostic assay may be used to distinguish between absence, presence, and excess expression of MPPS-1, and to monitor regulation of MPPS-1 levels during therapeutic intervention.

In one aspect, hybridization with PCR probes which are capable of detecting polynucleotide sequences, including genomic sequences, encoding MPPS-1 or closely related molecules, may be used to identify nucleic acid sequences which encode MPPS-1. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding MPPS-1, alleles, or related sequences.

Probes may also be used for the detection of related sequences, and should preferably contain at least 50% of the nucleotides from any of the MPPS-1 encoding sequences. The hybridization probes of the subject invention may be DNA or RNA and derived from the nucleotide sequence of SEQ ID NO:2 or from genomic sequence including promoter, enhancer elements, and introns of the naturally occurring MPPS-1.

Means for producing specific hybridization probes for DNAs encoding MPPS-1 include the cloning of nucleic acid sequences encoding MPPS-1 or MPPS-1 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding MPPS-1 may be used for the diagnosis of conditions or disorders which are associated with expression of MPPS-1. Examples of such conditions or disorders include smooth muscle disorders such as angina, anaphylactic shock, arrhythmias, asthma, cardiovascular shock, Cushing's syndrome, hypertension, hypoglycemia, myocardial infarction, migraine, and pheochromocytoma, and myopathies including cardiomyopathy, encephalopathy, epilepsy, Kearns-Sayre syndrome, lactic acidosis, myoclonic disorder, and ophthalmoplegia; neurological disorders such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder; and cancer such as adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding MPPS-1 may be used in Southern or northern analysis, dot blot, or other membrane-based technologies; in PCR technologies; or in dipstick, pin, ELISA assays or microarrays utilizing fluids or tissues from patient biopsies to detect altered MPPS-1 expression. Such qualitative or quantitative methods are well known in the art.

In a particular aspect, the nucleotide sequences encoding MPPS-1 may be useful in assays that detect activation or induction of various cancers, particularly those mentioned above. The nucleotide sequences encoding MPPS-1 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding MPPS-1 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of MPPS-1, a normal or standard profile for expression is established. This may be accomplished by combining body fluids or cell extracts taken from normal subjects, either animal or human, with a sequence, or a fragment thereof, which encodes MPPS-1, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding MPPS-1 may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of MPPS-1 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14:1675–1680) and Schena, M. et al. (1996; Proc. Natl. Acad. Sci. 93:10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode MPPS-1 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding MPPS-1 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, MPPS-1, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between MPPS-1 and the agent being tested, may be measured.

Another technique for drug screening which may be used provides for high throughput screening of compounds having suitable binding affinity to the protein of interest as described in published PCT application WO84/03564. In this method, as applied to MPPS-1 large numbers of different small test compounds are synthesized on a solid substrate, such as plastic pins or some other surface. The test compounds are reacted with MPPS-1, or fragments thereof, and washed. Bound MPPS-1 is then detected by methods well known in the art. Purified MPPS-1 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding MPPS-1 specifically compete with a test compound for binding MPPS-1. In this manner, the antibodies can be used to detect the presence of any peptide which shares one or more antigenic determinants with MPPS-1.

In additional embodiments, the nucleotide sequences which encode MPPS-1 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRAINOT14 cDNA Library Construction

The BRAINOT14 cDNA library was constructed from microscopically normal brain tissue obtained from a 40-year-old Caucasian female (specimen #0447A; Mayo Clinic, Rochester, Minn.) during cerebral meningeal excision following diagnosis of grade 4 (of 4) gemistocytic astrocytoma localized in the left frontal part of the brain. Prior to surgery the patient was also diagnosed with coma, epilepsy, and paralysis. The patient's history included a diagnosis of chronic nephritis.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7M CsCl cushion using an Beckman SW28 rotor in a Beckman L8–70M Ultracentrifuge (Beckman Instruments) for 18 hours at 25,000 rpm at ambient temperature. The RNA was extracted with acid phenol pH 4.7, precipitated using 0.3M sodium acetate and 2.5 volumes of ethanol, resuspended in RNAse-free water, and DNase treated at 37° C. RNA extraction and precipitation were repeated as before. The mRNA was then isolated using the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Cat. #18248–013; Gibco/BRL, Gaithersburg, Md.). cDNAs were fractionated on a Sepharose CL4B column (Cat. #275105–01; Pharmacia), and those cDNAs exceeding 400 bp were ligated into pINCY I. The plasmid pINCY I was subsequently transformed into DH5a ™ competent cells (Cat. #18258–012; Gibco/BRL).

II Isolation and Sequencing of cDNA Clones

Plasmid DNA was released from the cells and purified using the REAL Prep 96 Plasmid Kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36:290–300; Altschul et al. (1990) J. Mol. Biol. 215:403–410).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R. F. and T. F. Smith (1992; Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin, S. and S. F. Atschul (1993; Proc. Nat. Acad. Sci. 90:5873–7) and incorporated herein by reference, searches for matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

Incyte nucleotide sequences were searched against the GenBank databases for primate (pri), rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide).

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) *J. Mol. Evol.* 36:290–300; Altschul, S. F. et al. (1990) *J. Mol. Evol.* 215:403–410) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding MPPS-1 occurs. Abundance and percent abundance are also reported. Abundance directly reflects the number of times a particular transcript is represented in a cDNA library, and percent abundance is abundance divided by the total number of sequences examined in the cDNA library.

V Extension of MPPS-1 Encoding Polynucleotides

The nucleic acid sequence of the Incyte Clone 1593490 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1µl T4 polynucleotide kinase were added, and the mixture was incubated at room temperature for 2–3 hours or overnight at 16° C. Competent *E. coli* cells (in 40 µl of appropriate media) were transformed with 3 µl of ligation mixture and cultured in 80 µl of SOC medium (Sambrook et al., supra). After incubation for one hour at 37° C., the *E. coli* mixture was plated on Luria Bertani (LB)-agar (Sambrook et al., supra) containing 2× Carb. The following day, several colonies were randomly picked from each plate and cultured in 150 µl of liquid LB/2×Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). An aliquot containing 10$^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the MPPS-1 -encoding sequence, or any part thereof, is used to decrease or inhibit expression of naturally occurring MPPS-1. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of MPPS-1, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the MPPS-1-encoding transcript.

IX Expression of MPPS-1

Expression of MPPS-1 is accomplished by subcloning the cDNAs into appropriate vectors and transforming the vectors into host cells. In this case, the cloning vector is also used to express MPPS-1 in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of MPPS-1 into the bacterial growth media which can be used directly in the following assay for activity.

X Demonstration of MPPS-1 Activity

MPPS-1 activity is measured in reconstituted MPP by the hydrolysis of a signal peptide from a mitochondrial protein precursor (Kleiber, J. et al. (1990) Proc. Natl. Acad. Sci. 87:7978–82). MPPS-1 is first reconstituted with alpha-MPP to form MPP. The MPP is then incubated with $^{14}$C-labeled ornithine transcarbamylase precursor (pOTC) and MnCl$_2$ in a suitable buffer. pOTC is separated from the intermediate-sized form of OTC, lacking the leader peptide (iOTC), by SDS gel electrophoresis. The iOTC is visualized by autoradiography, cut out, and counted in a radioisotope counter. The amount of iOTC formed in the assay is proportional to the activity of MPPS-1 in the enzyme preparation.

XI Production of MPPS-1 Specific Antibodies

MPPS-1 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring MPPS-1 Using Specific Antibodies

Naturally occurring or recombinant MPPS-1 is substantially purified by immunoaffinity chromatography using antibodies specific for MPPS-1. An immunoaffinity column is constructed by covalently coupling MPPS-1 antibody to an activated chromatographic resin, such as CNBr-activated Sepharose (Pharmacia & Upjohn). After the coupling, the resin is blocked and washed according to the manufacturer's instructions.

Media containing MPPS-1 is passed over the immunoaffinity column, and the column is washed under conditions that allow the preferential absorbance of MPPS-1 (e.g., high ionic strength buffers in the presence of detergent). The column is eluted under conditions that disrupt antibody/MPPS-1 binding (eg, a buffer of pH 2–3 or a high concentration of a chaotrope, such as urea or thiocyanate ion), and MPPS-1 is collected.

XIII Identification of Molecules Which Interact with MPPS-1

MPPS-1 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled MPPS-1, washed and any wells with labeled MPPS-1 complex are assayed. Data obtained using different concentrations of MPPS-1 are used to calculate values for the number, affinity, and association of MPPS-1 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding the amino acid sequence of SEQ ID No:1.

2. A composition comprising the polynucleotide sequence of claim 1.

3. An isolated and purified polynucleotide sequence which is completely complementary to the polynucleotide sequence of claim 1.

4. An isolated and purified polynucleotide sequence comprising SEQ ID No:2.

5. An isolated and purified polynucleotide sequence which is completely complementary to the polynucleotide sequence of claim 4.

6. An expression vector containing the polynucleotide sequence of claim 1.

7. A host cell containing the vector of claim 6.

8. A method for producing a polypeptide comprising the amino acid sequence of SEQ ID No:1, the method comprising the steps of:

a) culturing the host cell of claim 7 under conditions suitable for the expression of the polypeptide; and b) recovering the polypeptide from the host cell culture.

9. A method for detecting a polynucleotide which encodes a mitochondrial processing peptidase subunit in a biological sample comprising the steps of:

a) hybridizing the polynucleotide of claim 3 to nucleic acid material of a biological sample, thereby forming a hybridization complex; and b) detecting said hybridization complex, wherein the presence of said complex correlates with the presence of a polynucleotide encoding the mitochondrial processing peptidase subunit in said biological sample.

10. The method of claim 9 wherein the nucleic acid material is amplified by the polymerase chain reaction prior to hybridization.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 489 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: BRAINOT14
        ( B ) CLONE: 1593490

( x i ) SEQUENCE DESCRIPTION: SEQ ID NO:1:

```
Met Ala Ala Ala Ala Ala Arg Val Val Leu Ser Ser Ala Ala Arg Arg
 1               5                  10                  15

Arg Leu Trp Gly Phe Ser Glu Ser Leu Leu Ile Arg Gly Ala Ala Gly
            20                  25                  30

Arg Ser Leu Tyr Phe Gly Glu Asn Arg Leu Arg Ser Thr Gln Ala Ala
        35                  40                  45

Thr Gln Val Val Leu Asn Val Pro Glu Thr Arg Val Thr Cys Leu Glu
    50                  55                  60

Ser Gly Leu Arg Val Ala Ser Glu Asp Ser Gly Leu Ser Thr Cys Thr
65                  70                  75                  80

Val Gly Leu Trp Ile Asp Ala Gly Ser Arg Tyr Glu Asn Glu Lys Asn
                85                  90                  95

Asn Gly Thr Ala His Phe Leu Glu His Met Ala Phe Lys Gly Thr Lys
            100                 105                 110

Lys Arg Ser Gln Leu Asp Leu Glu Leu Glu Ile Glu Asn Met Gly Ala
        115                 120                 125

His Leu Asn Ala Tyr Thr Ser Arg Glu Gln Thr Val Tyr Tyr Ala Lys
    130                 135                 140

Ala Phe Ser Lys Asp Leu Pro Arg Ala Val Glu Ile Leu Ala Asp Ile
145                 150                 155                 160

Ile Gln Asn Ser Thr Leu Gly Glu Ala Glu Ile Glu Arg Glu Arg Gly
                165                 170                 175
```

| | | | | | | | | | | | | | | |
|---|---|---|---|---|---|---|---|---|---|---|---|---|---|---|
|Val|Ile|Leu|Arg|Glu|Met|Gln|Glu|Val|Glu|Thr|Asn|Leu|Gln|Glu|Val|
| | | |180| | | |185| | | | |190| | |
|Val|Phe|Asp|Tyr|Leu|His|Ala|Thr|Ala|Tyr|Gln|Asn|Thr|Ala|Leu|Xaa|
| | |195| | | |200| | | |205| | | | |
|Arg|Thr|Ile|Phe|Gly|Pro|Thr|Glu|Asn|Ile|Lys|Ser|Ile|Ser|Arg|Lys|
| |210| | | |215| | | |220| | | | | | |
|Asp|Leu|Val|Asp|Tyr|Ile|Thr|Thr|His|Tyr|Lys|Gly|Pro|Arg|Ile|Val|
|225| | | | |230| | | |235| | | | |240| |
|Leu|Ala|Ala|Ala|Gly|Gly|Val|Ser|His|Asp|Glu|Leu|Leu|Asp|Leu|Ala|
| | | | |245| | | |250| | | | |255| | |
|Lys|Phe|His|Phe|Gly|Asp|Ser|Leu|Cys|Thr|His|Lys|Gly|Glu|Ile|Pro|
| | | |260| | | |265| | | | |270| | | |
|Ala|Leu|Pro|Pro|Cys|Lys|Phe|Thr|Gly|Ser|Glu|Ile|Arg|Val|Arg|Asp|
| | |275| | | | |280| | | |285| | | | |
|Asp|Lys|Met|Pro|Leu|Ala|His|Leu|Ala|Ile|Ala|Val|Glu|Ala|Val|Gly|
| |290| | | | |295| | | |300| | | | | |
|Trp|Ala|His|Pro|Asp|Thr|Ile|Cys|Leu|Met|Val|Ala|Asn|Thr|Leu|Ile|
|305| | | | |310| | | |315| | | | |320| |
|Gly|Asn|Trp|Asp|Arg|Ser|Phe|Gly|Gly|Gly|Met|Asn|Leu|Ser|Ser|Lys|
| | | |325| | | | |330| | | | |335| | |
|Leu|Ala|Gln|Leu|Thr|Cys|His|Gly|Asn|Leu|Cys|His|Ser|Phe|Gln|Ser|
| | |340| | | | |345| | | | |350| | | |
|Phe|Asn|Thr|Ser|Tyr|Thr|Asp|Thr|Gly|Leu|Trp|Gly|Leu|Tyr|Met|Val|
| |355| | | | |360| | | | |365| | | | |
|Cys|Glu|Ser|Ser|Thr|Val|Ala|Asp|Met|Leu|His|Val|Val|Gln|Lys|Glu|
|370| | | | |375| | | |380| | | | | | |
|Trp|Met|Arg|Leu|Cys|Thr|Ser|Val|Thr|Glu|Ser|Asp|Val|Ala|Arg|Ala|
|385| | | | |390| | | |395| | | | |400| |
|Arg|Asn|Leu|Leu|Lys|Thr|Asn|Met|Leu|Leu|Gln|Leu|Asp|Gly|Ser|Thr|
| | | |405| | | | |410| | | | |415| | |
|Pro|Ile|Cys|Glu|Asp|Ile|Gly|Arg|Gln|Met|Leu|Cys|Tyr|Asn|Arg|Arg|
| | |420| | | | |425| | | | |430| | | |
|Ile|Pro|Ile|Pro|Glu|Leu|Glu|Ala|Arg|Ile|Asp|Ala|Val|Asn|Ala|Glu|
| |435| | | | |440| | | |445| | | | | |
|Thr|Ile|Arg|Glu|Val|Cys|Thr|Lys|Tyr|Ile|Tyr|Asn|Arg|Ser|Pro|Ala|
|450| | | | |455| | | |460| | | | | | |
|Ile|Ala|Ala|Val|Gly|Pro|Ile|Lys|Gln|Leu|Pro|Asp|Phe|Lys|Gln|Ile|
|465| | | | |470| | | |475| | | | |480| |
|Arg|Ser|Asn|Met|Cys|Trp|Leu|Arg|Asp| | | | | | | |
| | | | |485| | | | | | | | | | | |

( 2 ) INFORMATION FOR SEQ ID NO:2:

( i ) SEQUENCE CHARACTERISTICS:
        ( A ) LENGTH: 1789 base pairs
        ( B ) TYPE: nucleic acid
        ( C ) STRANDEDNESS: single
        ( D ) TOPOLOGY: linear ( v i i ) IMMEDIATE SOURCE:
        ( A ) LIBRARY: BRAINOT14
        ( B ) CLONE: 1593490

( x i ) SEQUENCE DESCRIPTION: SEQ ID NO:2:

```
CCTCTACCTT   CCTTCTAGCA   GAAATGGCGG   CTGCGGCGGC   TCGAGTGGTG   TTGTCATCCG      60

CGGCGCGGCG   GCGGCTCTGG   GGTTTCAGCG   AGAGTCTTCT   AATCCGAGGC   GCTGCGGGAC     120

GGTCATTATA   TTTTGGAGAG   AACAGATTAA   GAAGTACACA   GGCTGCTACC   CAAGTTGTTC     180
```

-continued

```
TGAATGTTCC  TGAAACAAGA  GTAACATGTT  TAGAAAGTGG  ACTCAGAGTA  GCTTCGGAAG    240

ACTCTGGGCT  CTCAACATGC  ACAGTTGGAC  TCTGGATTGA  TGCTGGAAGT  AGATACGAAA    300

ATGAGAAGAA  CAATGGAACA  GCACACTTTC  TGGAGCATAT  GGCTTTCAAG  GGCACCAAGA    360

AGAGATCCCA  GTTAGATCTG  GAACTTGAGA  TTGAAAATAT  GGGTGCTCAT  CTCAATGCCT    420

ATACCTCCAG  AGAGCAGACT  GTATACTATG  CCAAAGCATT  CTCTAAAGAC  TTGCCAAGAG    480

CTGTAGAAAT  TCTTGCTGAT  ATAATACAAA  ACAGCACATT  GGGAGAAGCA  GAGATTGAAC    540

GTGAGCGTGG  AGTAATCCTT  AGAGAGATGC  AGGAAGTTGA  AACCAATTTA  CAAGAAGTTG    600

TTTTTGATTA  TCTTCATGCC  ACAGCTTATC  AAAATACTGC  ACTTTGACGG  ACAATTTTG     660

GACCAACTGA  AAATATCAAA  TCTATAAGTC  GTAAGGACTT  AGTGGATTAT  ATAACCACAC    720

ATTATAAGGG  GCCAAGAATA  GTGCTTGCTG  CTGCTGGAGG  TGTTTCCCAT  GATGAATTGC    780

TTGACTTAGC  AAAGTTTCAT  TTCGGTGACT  CTTTATGCAC  ACACAAAGGA  GAAATACCAG    840

CTCTGCCTCC  CTGCAAATTC  ACAGGAAGTG  AGATTCGTGT  GAGGGATGAC  AAGATGCCTT    900

TGGCGCACCT  TGCAATAGCT  GTTGAAGCTG  TTGGTTGGGC  ACATCCAGAT  ACAATCTGTC    960

TCATGGTTGC  AAACACGCTG  ATTGGCAACT  GGGATCGCTC  TTTTGGGGGA  GGAATGAATT   1020

TATCTAGCAA  GCTGGCCCAG  CTCACTTGTC  ATGGCAATCT  TTGCCATAGC  TTTCAGTCTT   1080

TCAACACTTC  CTACACAGAT  ACAGGATTAT  GGGGACTGTA  TATGGTTTGT  GAATCATCCA   1140

CTGTTGCAGA  CATGCTACAT  GTTGTTCAAA  AAGAATGGAT  GCGACTCTGT  ACAAGTGTCA   1200

CAGAAAGTGA  TGTTGCACGA  GCCAGAAATC  TTCTGAAAAC  AAACATGTTG  TTGCAGCTTG   1260

ATGGTTCAAC  TCCAATTTGT  GAAGATATTG  GTAGGCAAAT  GTTATGCTAT  AATAGAAGGA   1320

TTCCCATCCC  TGAGCTTGAA  GCAAGAATTG  ATGCTGTGAA  TGCTGAGACA  ATTCGAGAAG   1380

TATGTACCAA  ATACATTTAT  AATAGGAGTC  CAGCTATTGC  TGCTGTTGGT  CCCATTAAGC   1440

AACTACCAGA  TTTTAAACAG  ATACGCAGTA  ACATGTGTTG  GCTTCGTGAT  TAAAATGCTC   1500

CTAATCAAGA  TTGTTTGAAC  ACATGTATTT  ATAAAACAGA  GCTAGAGAAA  ATAAAAATG    1560

AACATGTATA  TACATTTGGA  AATTTGAATT  AAATACTGTA  TCATACTTTC  AAAGGATAAA   1620

AAGACTACCC  CTCTGAAGGT  TGTTTTGTAT  TAATGGTCAG  TCTTTGTTCT  CTGAGAAATT   1680

ATGTTGGAAG  CAGCATACTT  TCAAATTATT  ACCATGAGTA  TAATTTTAAG  AATGAAAATG   1740

TTTACAGTAT  TTTCAGTTTT  ATTATAAAAA  TGCACACACA  AAAAAAAA              1789
```

(2) INFORMATION FOR SEQ ID NO:3:

(i) SEQUENCE CHARACTERISTICS:
        (A) LENGTH: 489 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 294589

(xi) SEQUENCE DESCRIPTION: SEQ ID NO:3:

```
Met  Ala  Ala  Ala  Ala  Val  Ser  Arg  Thr  Leu  Leu  Pro  Val  Ala  Gly  Arg
 1              5                        10                       15

Arg  Leu  Trp  Gly  Phe  Thr  Arg  Arg  Leu  Pro  Leu  Arg  Ala  Ala  Ala  Ala
            20                       25                       30

Gln  Pro  Leu  Tyr  Phe  Gly  Gly  Asp  Arg  Leu  Arg  Ser  Thr  Gln  Ala  Ala
        35                       40                       45

Pro  Gln  Val  Val  Leu  Asn  Val  Pro  Glu  Thr  Gln  Val  Thr  Cys  Leu  Glu
```

```
                  50                        55                        60
Asn  Gly  Leu  Arg  Val  Ala  Ser  Glu  Asn  Ser  Gly  Ile  Ser  Thr  Cys  Thr
 65                       70                       75                       80

Val  Gly  Leu  Trp  Ile  Asp  Ala  Gly  Ser  Arg  Tyr  Glu  Asn  Glu  Lys  Asn
                     85                       90                       95

Asn  Gly  Thr  Ala  His  Phe  Leu  Glu  His  Met  Ala  Phe  Lys  Gly  Thr  Lys
                    100                      105                      110

Lys  Arg  Ser  Gln  Leu  Asp  Leu  Glu  Leu  Glu  Ile  Glu  Asn  Met  Gly  Ala
               115                      120                      125

His  Leu  Asn  Ala  Tyr  Thr  Ser  Arg  Glu  Gln  Thr  Val  Tyr  Tyr  Ala  Lys
          130                      135                      140

Ala  Phe  Ser  Lys  Asp  Leu  Pro  Arg  Ala  Val  Glu  Ile  Leu  Ala  Asp  Ile
145                      150                      155                      160

Ile  Gln  Asn  Ser  Thr  Leu  Gly  Glu  Ala  Glu  Ile  Glu  Arg  Glu  Arg  Gly
                    165                      170                      175

Val  Ile  Leu  Arg  Glu  Met  Gln  Glu  Val  Glu  Thr  Asn  Leu  Gln  Glu  Val
               180                      185                      190

Val  Phe  Asp  Tyr  Leu  His  Ala  Thr  Ala  Tyr  Gln  Asn  Thr  Ala  Leu  Gly
          195                      200                      205

Arg  Thr  Ile  Leu  Gly  Pro  Thr  Glu  Asn  Ile  Lys  Ser  Ile  Ser  Arg  Lys
     210                      215                      220

Asp  Leu  Val  Asp  Tyr  Ile  Thr  Thr  His  Tyr  Lys  Gly  Pro  Arg  Ile  Val
225                      230                      235                      240

Leu  Ala  Ala  Ala  Gly  Gly  Val  Cys  His  Asn  Glu  Leu  Leu  Glu  Leu  Ala
                    245                      250                      255

Lys  Phe  His  Phe  Gly  Asp  Ser  Leu  Cys  Ala  His  Lys  Gly  Asp  Val  Pro
               260                      265                      270

Ala  Leu  Pro  Pro  Cys  Lys  Phe  Thr  Gly  Ser  Glu  Ile  Arg  Val  Arg  Asp
          275                      280                      285

Asp  Lys  Met  Pro  Leu  Ala  His  Leu  Ala  Val  Ala  Ile  Glu  Ala  Val  Gly
     290                      295                      300

Trp  Thr  His  Pro  Asp  Thr  Ile  Arg  Leu  Met  Val  Ala  Asn  Thr  Leu  Ile
305                      310                      315                      320

Gly  Asn  Trp  Asp  Arg  Ser  Phe  Gly  Gly  Gly  Met  Asn  Leu  Ser  Ser  Lys
                    325                      330                      335

Leu  Ala  Gln  Leu  Thr  Cys  His  Gly  Asn  Leu  Cys  His  Ser  Phe  Gln  Ser
               340                      345                      350

Phe  Asn  Thr  Ser  Tyr  Thr  Asp  Thr  Gly  Leu  Trp  Gly  Leu  Tyr  Met  Val
          355                      360                      365

Cys  Glu  Gln  Ala  Thr  Val  Ala  Asp  Met  Leu  His  Ala  Val  Gln  Lys  Glu
     370                      375                      380

Trp  Met  Arg  Leu  Cys  Thr  Ala  Val  Ser  Glu  Ser  Glu  Val  Ala  Arg  Ala
385                      390                      395                      400

Lys  Asn  Leu  Leu  Lys  Thr  Asn  Met  Leu  Leu  Gln  Leu  Asp  Gly  Ser  Thr
                    405                      410                      415

Pro  Ile  Cys  Glu  Asp  Ile  Gly  Arg  Gln  Met  Leu  Cys  Tyr  Asn  Arg  Arg
               420                      425                      430

Ile  Pro  Ile  Pro  Glu  Leu  Glu  Ala  Arg  Ile  Asp  Ala  Val  Asp  Ala  Glu
          435                      440                      445

Met  Val  Arg  Glu  Val  Cys  Thr  Lys  Tyr  Ile  Tyr  Gly  Lys  Ser  Pro  Ala
     450                      455                      460

Ile  Ala  Ala  Leu  Gly  Pro  Ile  Glu  Arg  Leu  Pro  Asp  Phe  Asn  Gln  Ile
465                      470                      475                      480
```

Cys Ser Asn Met Arg Trp Thr Arg Asp
                485

(2) INFORMATION FOR SEQ ID NO:4:

(i) SEQUENCE CHARACTERISTICS:
    (A) LENGTH: 480 amino acids
    (B) TYPE: amino acid
    (C) STRANDEDNESS: single
    (D) TOPOLOGY: linear (vii) IMMEDIATE SOURCE:
    (A) LIBRARY: GenBank
    (B) CLONE: 1082896

(xi) SEQUENCE DESCRIPTION: SEQ ID NO:4:

Met Ala Ala Ser Val Val Cys Arg Ala Ala Thr Ala Gly Ala Gln Val
 1               5                  10                  15

Leu Leu Arg Ala Arg Arg Ser Pro Ala Leu Leu Arg Thr Pro Ala Leu
            20                  25                  30

Arg Ser Thr Ala Thr Phe Ala Gln Ala Leu Gln Phe Val Pro Glu Thr
            35                  40                  45

Gln Val Ser Leu Leu Asp Asn Gly Leu Arg Val Ala Ser Glu Gln Ser
        50                  55                  60

Ser Gln Pro Thr Cys Thr Val Gly Val Trp Ile Asp Val Gly Ser Arg
65                  70                  75                  80

Phe Glu Thr Glu Lys Asn Asn Gly Ala Gly Tyr Phe Leu Glu His Leu
                85                  90                  95

Ala Phe Lys Gly Thr Lys Asn Arg Pro Gly Ser Ala Leu Glu Lys Glu
            100                 105                 110

Val Glu Ser Met Gly Ala His Leu Asn Ala Tyr Ser Thr Arg Glu His
            115                 120                 125

Thr Ala Tyr Tyr Ile Lys Ala Leu Ser Lys Asp Leu Pro Lys Ala Val
        130                 135                 140

Glu Leu Leu Gly Asp Ile Val Gln Asn Cys Ser Leu Glu Asp Ser Gln
145                 150                 155                 160

Ile Glu Lys Glu Arg Asp Val Ile Leu Arg Glu Met Gln Glu Asn Asp
                165                 170                 175

Ala Ser Met Arg Asp Val Val Phe Asn Tyr Leu His Ala Thr Ala Phe
            180                 185                 190

Gln Gly Thr Pro Leu Ala Gln Ala Val Glu Gly Pro Ser Glu Asn Val
        195                 200                 205

Arg Lys Leu Ser Arg Ala Asp Leu Thr Glu Tyr Leu Ser Thr His Tyr
210                 215                 220

Lys Ala Pro Arg Met Val Leu Ala Ala Ala Gly Gly Val Glu His Gln
225                 230                 235                 240

Gln Leu Leu Asp Leu Ala Gln Lys His Leu Gly Gly Ile Pro Trp Thr
                245                 250                 255

Tyr Ala Glu Asp Ala Val Pro Thr Leu Thr Pro Cys Arg Phe Thr Gly
            260                 265                 270

Ser Glu Ile Arg His Arg Asp Asp Ala Leu Pro Phe Ala His Val Ala
        275                 280                 285

Ile Ala Val Glu Gly Pro Gly Trp Ala Ser Pro Asp Ser Val Ala Leu
290                 295                 300

Gln Val Ala Asn Ala Ile Ile Gly His Tyr Asp Cys Thr Tyr Gly Gly
305                 310                 315                 320

Gly Val His Leu Ser Ser Pro Leu Ala Ser Gly Ala Val Ala Asn Lys
                325                 330                 335

| | | | | | | | | | | | | | | | |
|---|---|---|---|---|---|---|---|---|---|---|---|---|---|---|---|
| Leu | Cys | Gln | Ser 340 | Phe | Gln | Thr | Phe | Ser 345 | Ile | Cys | Tyr | Ala | Glu 350 | Thr | Gly |
| Leu | Leu | Gly 355 | Ala | His | Phe | Val | Cys 360 | Asp | Arg | Met | Lys | Ile 365 | Asp | Asp | Met |
| Met | Phe 370 | Val | Leu | Gln | Gly | Gln 375 | Trp | Met | Arg | Leu | Cys 380 | Thr | Ser | Ala | Thr |
| Glu 385 | Ser | Glu | Val | Ala | Arg 390 | Gly | Lys | Asn | Ile | Leu 395 | Arg | Asn | Ala | Leu | Val 400 |
| Ser | His | Leu | Asp | Gly 405 | Thr | Thr | Pro | Val | Cys 410 | Glu | Asp | Ile | Gly | Arg 415 | Ser |
| Leu | Leu | Thr | Tyr 420 | Gly | Arg | Arg | Ile | Pro 425 | Leu | Ala | Glu | Trp | Glu 430 | Ser | Arg |
| Ile | Ala | Glu 435 | Val | Asp | Ala | Ser | Val 440 | Val | Arg | Glu | Ile | Cys 445 | Ser | Lys | Tyr |
| Ile | Tyr 450 | Asp | Gln | Cys | Pro | Ala 455 | Val | Ala | Gly | Tyr | Gly 460 | Pro | Ile | Glu | Gln |
| Leu 465 | Pro | Asp | Tyr | Asn | Arg 470 | Ile | Arg | Ser | Gly | Met 475 | Phe | Trp | Leu | Arg | Phe 480 |